United States Patent
Dejuan, Jr. et al.

(10) Patent No.: US 7,220,225 B2
(45) Date of Patent: *May 22, 2007

(54) INTRAOCULAR RADIOTHERAPY TREATMENT

(75) Inventors: Eugene Dejuan, Jr., LaCanada, CA (US); Paul Hallen, Ft. Worth, TX (US)

(73) Assignee: RetinaLabs, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/407,498

(22) Filed: Apr. 20, 2006

(65) Prior Publication Data

US 2006/0189838 A1 Aug. 24, 2006

Related U.S. Application Data

(63) Continuation of application No. 11/282,408, filed on Nov. 18, 2005, which is a continuation of application No. 11/075,098, filed on Mar. 8, 2005, which is a continuation of application No. 09/790,486, filed on Feb. 22, 2001, now Pat. No. 6,875,165.

(51) Int. Cl.
*A61N 5/00* (2006.01)

(52) U.S. Cl. .............. 600/3; 600/8; 604/521; 606/4; 128/898

(58) Field of Classification Search .......... 600/1–8; 604/20, 21, 521, 294; 606/4
See application file for complete search history.

(56) References Cited

U.S. PATENT DOCUMENTS

| 839,061 | A | 12/1906 | Farjas |
|---|---|---|---|
| 2,517,568 | A | 8/1950 | Hissong |
| 2,559,793 | A | 7/1951 | Pregel |
| 4,662,869 | A | 5/1987 | Wright |
| 4,891,165 | A | 1/1990 | Suthanthiran |
| 4,996,159 | A | 2/1991 | Glaser |
| 5,203,353 | A | 4/1993 | Easley et al. |
| 5,342,283 | A | 8/1994 | Good |
| 5,422,926 | A | 6/1995 | Smith et al. |
| 5,425,730 | A | 6/1995 | Luloh |
| 5,426,662 | A | 6/1995 | Mefferd et al. |
| 5,431,907 | A | 7/1995 | Abelson et al. |
| 5,487,725 | A * | 1/1996 | Peyman .......... 604/22 |
| 5,596,011 | A | 1/1997 | Repine et al. |
| 5,637,073 | A | 6/1997 | Freire |

(Continued)

FOREIGN PATENT DOCUMENTS

DE    19933284    1/2001

(Continued)

OTHER PUBLICATIONS

Dig. J. Ophthalmol., "Development in Retinal Cell Transplants," 2001, vol. 7(2). From: http://www.medscape.com/viewarticle/408963_print.

(Continued)

*Primary Examiner*—Ramesh Krishnamurthy

(57) ABSTRACT

A surgical device for localized delivery of beta radiation in surgical procedures, particularly ophthalmic procedures. Preferred surgical devices include a cannula with a beta radiotherapy emitting material at the distal end of the cannula. The surgical device is particularly suitable for use in the treatment of treat Age Related Macular Degeneration (AMD).

38 Claims, 2 Drawing Sheets

U.S. PATENT DOCUMENTS

| | | | |
|---|---|---|---|
| 5,651,783 | A | 7/1997 | Reynard |
| 5,688,220 | A | 11/1997 | Verin et al. |
| 5,707,332 | A | 1/1998 | Weinberger |
| 5,729,583 | A | 3/1998 | Tang et al. |
| 5,830,173 | A * | 11/1998 | Avery et al. ................ 604/9 |
| 5,854,822 | A | 12/1998 | Chornenky et al. |
| 5,904,144 | A | 5/1999 | Hamming et al. |
| 5,976,106 | A | 11/1999 | Verin et al. |
| 6,004,279 | A | 12/1999 | Crowley et al. |
| 6,024,690 | A | 2/2000 | Lee et al. |
| 6,030,333 | A | 2/2000 | Sioshansi et al. |
| 6,041,252 | A | 3/2000 | Walker et al. |
| 6,050,930 | A | 4/2000 | Teirstein |
| 6,069,938 | A | 5/2000 | Chornenky et al. |
| 6,071,227 | A | 6/2000 | Popowski et al. |
| 6,074,338 | A | 6/2000 | Popowski et al. |
| 6,095,966 | A | 8/2000 | Chornenky et al. |
| 6,102,844 | A | 8/2000 | Ravins et al. |
| 6,108,402 | A | 8/2000 | Chornenky |
| 6,111,932 | A | 8/2000 | Dinsmore |
| 6,134,294 | A | 10/2000 | Gibbs |
| 6,146,322 | A | 11/2000 | Papirov et al. |
| 6,149,931 | A | 11/2000 | Schwartz et al. |
| 6,162,165 | A | 12/2000 | Apple et al. |
| 6,164,281 | A | 12/2000 | Zhao |
| 6,181,770 | B1 | 1/2001 | Ciravolo et al. |
| 6,195,411 | B1 | 2/2001 | Dinsmore |
| 6,198,804 | B1 | 3/2001 | Dinsmore |
| 6,210,315 | B1 | 4/2001 | Andrews et al. |
| 6,231,494 | B1 | 5/2001 | Verin et al. |
| 6,245,047 | B1 | 6/2001 | Feda et al. |
| 6,258,019 | B1 | 7/2001 | Verin et al. |
| 6,264,599 | B1 | 7/2001 | Slater et al. |
| 6,284,751 | B1 | 9/2001 | Aiello et al. |
| 6,285,735 | B1 | 9/2001 | Sliski et al. |
| 6,289,079 | B1 | 9/2001 | Chornenky et al. |
| 6,293,899 | B1 | 9/2001 | Sioshansi et al. |
| 6,299,054 | B1 | 10/2001 | Gibbs, Jr. |
| 6,301,328 | B1 | 10/2001 | Sliski et al. |
| 6,302,581 | B1 | 10/2001 | Sliski et al. |
| 6,312,393 | B1 | 11/2001 | Abreu |
| 6,320,932 | B2 | 11/2001 | Dinsmore |
| 6,320,935 | B1 | 11/2001 | Shinar et al. |
| 6,338,709 | B1 | 1/2002 | Geoffrion et al. |
| 6,347,244 | B1 | 2/2002 | Dubnack |
| 6,359,963 | B1 | 3/2002 | Cash |
| 6,377,846 | B1 | 4/2002 | Chornenky et al. |
| 6,387,035 | B1 | 5/2002 | Jung, Jr. et al. |
| 6,395,294 | B1 | 5/2002 | Peyman |
| 6,409,943 | B1 | 6/2002 | Lavie et al. |
| 6,415,016 | B1 | 7/2002 | Chornenky et al. |
| 6,416,457 | B1 | 7/2002 | Urick et al. |
| 6,419,621 | B1 | 7/2002 | Sioshansi et al. |
| 6,421,416 | B1 | 7/2002 | Sliski et al. |
| 6,433,012 | B1 | 8/2002 | Tuse et al. |
| 6,436,026 | B1 | 8/2002 | Sioshansi et al. |
| 6,438,206 | B1 | 8/2002 | Shinar et al. |
| 6,443,881 | B1 | 9/2002 | Finger |
| 6,443,976 | B1 | 9/2002 | Flower et al. |
| 6,458,068 | B1 | 10/2002 | Ellard et al. |
| 6,465,954 | B1 | 10/2002 | Kerslick et al. |
| 6,473,491 | B2 | 10/2002 | Chornenky et al. |
| 6,480,567 | B1 | 11/2002 | Feda et al. |
| 6,491,619 | B1 | 12/2002 | Trauthen et al. |
| 6,496,561 | B1 | 12/2002 | Meyer et al. |
| 6,546,077 | B2 | 4/2003 | Chornenky et al. |
| 6,551,291 | B1 | 4/2003 | de Juan, Jr. et al. |
| 6,579,256 | B2 | 6/2003 | Hughes |
| 6,676,590 | B1 | 1/2004 | Urick et al. |
| 6,676,607 | B2 | 1/2004 | de Juan, Jr. et al. |
| 6,692,759 | B1 | 2/2004 | Wong et al. |
| 6,719,750 | B2 * | 4/2004 | Varner et al. ................ 604/289 |
| 6,771,737 | B2 | 8/2004 | Kerslick et al. |
| 6,799,075 | B1 | 9/2004 | Chornenky et al. |
| 6,810,109 | B2 | 10/2004 | Chornenky et al. |
| 6,866,624 | B2 | 3/2005 | Chornenky et al. |
| 6,875,165 | B2 | 4/2005 | de Juan, Jr. et al. |
| 6,914,960 | B2 | 7/2005 | Swanson et al. |
| 2001/0002427 | A1 | 5/2001 | Verin et al. |
| 2001/0009970 | A1 | 7/2001 | Chornenky et al. |
| 2001/0016027 | A1 | 8/2001 | Dinsmore |
| 2001/0021382 | A1 | 9/2001 | Ferrara et al. |
| 2001/0027261 | A1 | 10/2001 | Ciezki et al. |
| 2001/0036955 | A1 | 11/2001 | Gerrilsen et al. |
| 2001/0050971 | A1 | 12/2001 | Feda et al. |
| 2002/0015957 | A1 | 2/2002 | Hageman et al. |
| 2002/0021784 | A1 | 2/2002 | Chornenky et al. |
| 2002/0040015 | A1 | 4/2002 | Miller et al. |
| 2002/0049247 | A1 | 4/2002 | Chen |
| 2002/0054664 | A1 | 5/2002 | Tiren |
| 2002/0054665 | A1 | 5/2002 | Tiren |
| 2002/0072494 | A1 | 6/2002 | Cao |
| 2002/0090053 | A1 | 7/2002 | Chornenky et al. |
| 2002/0106055 | A1 | 8/2002 | Cash |
| 2002/0110220 | A1 | 8/2002 | Shen et al. |
| 2002/0115902 | A1 | 8/2002 | de Juan, Jr. et al. |
| 2002/0146090 | A1 | 10/2002 | Chornenky et al. |
| 2002/0156003 | A1 | 10/2002 | Lorens et al. |
| 2002/0160954 | A1 | 10/2002 | Hageman et al. |
| 2002/0160979 | A1 | 10/2002 | Banerjee et al. |
| 2002/0183253 | A1 | 12/2002 | Brazzell et al. |
| 2002/0183302 | A1 | 12/2002 | Strong et al. |
| 2002/0193326 | A1 | 12/2002 | Sukhalme |
| 2003/0179854 | A1 | 9/2003 | Jaafar |
| 2004/0218721 | A1 | 11/2004 | Chornenky et al. |
| 2004/0218724 | A1 | 11/2004 | Chornenky et al. |
| 2005/0177019 | A1 | 8/2005 | De Juan, Jr. et al. |
| 2006/0142629 | A1 | 6/2006 | de Juan et al. |

FOREIGN PATENT DOCUMENTS

| | | |
|---|---|---|
| GB | 1211316 | 11/1970 |
| WO | WO 98/01179 | 1/1998 |
| WO | WO 00/33916 | 12/1998 |
| WO | WO 01/43826 | 6/2001 |

OTHER PUBLICATIONS

UIC Office of Technology and Management, "Intraocular Brachytherapy Device," 2003, (2 Pages). From: http://www.vpted.uillinois.edu/Events/iemerging/COAs/Brachytherapy COA_2.pdf.

Finger, et al., "Palladum 103 Ophthalmic Plaque Radiotherapy", Arch Ophthalmol-vol. 109 Nov. 1991 (pp. 1610-1613).

Finger, et al., "Palladium-103 versus Iodine-125 for Ophthalmic Plaque Radiotherapy" Int. J. Radiation Oncology Biol. Phys. vol. 27 (pp. 849-854), 1993.

Finger, et al., Ophthalmic Plaque Radiotherapy for Age-related Macular Degeneration Associated with Subretinal Neovascularization American Journal of Ophthalmology, vol. 127, No. 2, 1999 (pp. 170-177).

Moore, R.F., Choroidal sarcoma treated by the intraocular insertion of radon seeds, Apr. 1930, The British Journal of Ophthalmology, vol. 14, pp. 145-152.

\* cited by examiner

US 7,220,225 B2

INTRAOCULAR RADIOTHERAPY TREATMENT

This application is a continuation of U.S. application Ser. No. 11/282,408, filed Nov. 18, 2005, which is a continuation of U.S. application Ser. No. 11/075,098, filed on Mar. 8, 2005, which is a continuation of U.S. application Ser. No. 09/790,486, filed on Feb. 22, 2001, now U.S. Pat. No. 6,875,165, all of which are hereby incorporated herein by reference.

The present invention relates to a device and method for localized delivery of beta radiation in surgical procedures, particularly ophthalmic procedures. More particularly, the present invention relates to a device and method for localized delivery of beta radiation to treat Age Related Macular Degeneration (AMD).

BACKGROUND

The slow, progressive loss of central vision is known as macular degeneration. Macular degeneration affects the macula, a small portion of the retina. The retina is a fine layer of light-sensing nerve cells that covers the inside back portion of the eye. The macula is the central, posterior part of the retina and contains the largest concentration of photoreceptors. The macula is typically 5 to 6 mm in diameter, and its central portion is known as the fovea. While all parts of the retina contribute to sight, only the macula provides the sharp, central vision that is required to see objects clearly and for daily activities including reading and driving Macular degeneration is generally caused by age (Age Related Macular Degeneration, "AMD") or poor circulation in the eyes. Smokers and individuals with circulatory problems have an increased risk for developing the condition.

AMD is the leading cause of blindness in people older than 50 years in developed countries. Between the ages of 52–64 approximately 2% of the population are affected. This rises to an astounding 28% over the age of 75.

The two forms of macular degeneration are known as "wet" and "dry" macular degeneration.

Dry macular degeneration blurs the central vision slowly over time. Individuals with this form of macular degeneration may experience a dimming or distortion of vision that is particularly noticeable when trying to read. In dry macular degeneration, yellowish deposits called drusen develop beneath the macula. Drusen are accumulations of fatty deposits, and most individuals older than 50 years have at least one small druse. These fatty deposits are usually carried away by blood vessels that transport nutrients to the retina. However, this process is diminished in macular degeneration and the deposits build up. Dry macular degeneration may also result when the layer of light-sensitive cells in the macula becomes thinner as cells break down over time. Generally, a person with dry form macular degeneration in one eye eventually develops visual problems in both eyes. However, dry macular degeneration rarely causes total loss of reading vision.

Wet macular degeneration (the neovascular form of the disease) is more severe than dry macular degeneration. The loss of vision due to wet macular degeneration also comes much more quickly than dry macular degeneration. In this form of the disease, unwanted new blood vessels grow beneath the macula (Choroidal Neo-Vascularization (CNV) endothelial cells). These choroidal blood vessels are fragile and leak fluid and blood, which causes separation of tissues and damages light sensitive cells in the retina. Individuals with this form of macular degeneration typically experience noticeable distortion of vision such as, for example, seeing straight lines as wavy, and seeing blank spots in their field of vision. Early diagnosis of this form of macular degeneration is vital. If the leakage and bleeding from the choroidal blood vessels is allowed to continue, much of the nerve tissue in the macula may be killed or damaged, and such damage cannot be repaired because the nerve cells of the macula do not grow back once they have been destroyed. While wet AMD comprises only about 20% of the total AMD cases, it is responsible for approximately 90% of vision loss attributable to AMD.

Currently, Photo-Dynamic Therapy (PDT) is used to treat individuals with wet macular degeneration. During PDT, a photo-sensitive drug is first delivered to the patient's system, typically by injecting the drug into the patient's bloodstream through a vein. The photo-sensitive drug attaches to molecules in the blood called lipoproteins. Because the choroidal blood vessels require a greater amount of lipoproteins than normal vessels, the drug is delivered more quickly and in higher concentrations to the choroidal blood vessels. Next, a non-thermal diode laser light is aimed into the eye to activate the photo-sensitive drug. The activated drug subsequently causes the conversion of normal oxygen found in tissue to a highly energized form called "singlet oxygen." The singlet oxygen, in turn, causes cell death by disrupting normal cellular functions, resulting in the closure of the choroidal blood vessels while leaving normal vessels still functional. While PDT cannot restore vision, it reduces the risk of vision loss by restricting the growth of abnormal choroidal blood vessels.

Laser therapy ("Laser Photocoagulation"), as opposed to Photo-Dynamic Therapy (PDT), uses heat. Basically, a "hot" laser is aimed at the choroidal blood vessels, resulting in the formation of heat when the laser contacts the vessels. This stops the growth, leakage, and bleeding of the choroidal blood vessels. However, the laser destroys surrounding healthy tissue in the process (collateral damage). Further, the "hot" laser forms scars, which may cause blind spots.

PDT, thus, is particularly advantageous because it does not use heat, so less collateral damage results, and the procedure can be repeated as many times as necessary. However, while PDT has shown some efficacy, the population of patients in which it shows efficacy is small (less than 20%). Furthermore, PDT does not typically restore lost vision, but rather, only slows the progression of vision loss. In the attempt to design a selective disruption therapy, it appears that PDT, although groundbreaking, is not aggressive enough to provide satisfying results for affected patients.

Radiation is a promising medical technology that may be effective for the treatment of choroidal neovascularization due to age related macular degeneration. There are basically three types of nuclear radiation: Alpha, Beta, and Gamma.

An alpha particle is simply a helium nucleus. It has the lowest power, penetration, and danger associated with it of the three types of radiation. Several sheets of paper would serve as a shield against alpha radiation.

Gamma radiation is the most powerful, most penetrating, and most dangerous type of radiation. Gamma radiation is an energy wave, not just a particle. Gamma sources are photons. Several meters of rock or many centimeters of lead are required to shield gamma radiation.

Gamma radiotherapy has been shown to be effective in vascular radiation therapy, particularly for the treatment of in-stent restenosis. Randomized data from the Scripps Trial (*The SCRIPPS Trial—Catheter-Based Radiotherapy to*

*Inhibit Coronary Restenosis*; J Invas Cardiol 12(6):330–332 (2000) a randomized, double blind, placebo-controlled study demonstrated a reduction in restenosis rates from 54% in the placebo group to 17% in patients treated with gamma radiation ($^{192}$Ir). Gamma sources penetrate human tissues deeply. This makes gamma energy ideal for treating large vessels. Gamma sources have been used in the clinical arena for decades and hospital radiotherapy departments have significant years of experiences using gamma sources.

There are, however, numerous disadvantages to using gamma sources. Photons are not blocked by the "usual" lead shields. A 1 inch lead shield is required. This is usually provided in the form of a very cumbersome heavy lead device attached to rollers that allow it to be wheeled into the catheterization laboratory. Due to the presence of deeply penetrating ionizing radiation, when high-energy gamma radiation is used in the catheterization laboratory, the procedure room must be cleared of all "nonessential" personnel. The patient is observed from a "control room" which is protected by lead shielding. Also, the patient receives more radiation from a gamma radiation procedure as compared to other radiation procedures. The radiation oncologist, who delivers the actual radiation sources, also receives additional radiation exposure. This problem of radiation exposure in the catheterization laboratory environment limits the maximal specific activity of the radiation sources. If the sources are of very high activity, the exposure to health care personnel in the control room will be higher than background exposure. This would be unacceptable. To circumvent this problem, lower specific activity sources must be used. This requires a long dwell time (8 to 20 minutes) to achieve therapeutic doses.

SUMMARY OF THE INVENTION

The present invention provides new surgical devices and methods for use thereof. Devices and methods of the invention are particularly useful for treatment of eye disorders such as Age Related Macular Degeneration More particularly, the present invention provides a device for localized delivery of beta radiation during surgical procedures and methods of use thereof. The device is particularly suitable for the localized delivery of beta radiation for the treatment of macular degeneration. The device delivers beta radiation to the affected sub-macular region afflicted with the condition.

Beta radiation is a high-speed electron. A typical source of beta radiation may be, for example, radioisotope Phosphorus 32 ($^{32}$P). Beta source electrons only penetrate 1 to 2 mm into human tissue. Even thick plastics easily shield beta energy. The fact that exposure from beta sources is limited allows the specific activity to be much higher than that of gamma sources. This translates into very short dwell times, for example, approximately 3 to 8 minutes of exposure is estimated for ophthalmic applications using a beta source, as opposed to the longer long dwell time associated with the use of a gamma source (8 to 20 minutes). Radiation safety concerns surrounding the use of beta sources are vastly reduced compared to that of gamma radiation. Health care personnel are able to remain in the operating room and additional exposure to the patient and surgeon is negligible. The dose of beta radiation received during macular radiotherapy will be less than that received during a conventional chest x-ray. We have found that beta radiotherapy can be an optimal balance of power, penetration, and safety for many medical applications and specifically for the treatment of choroidal neo-vascularization (CNV) caused by AMD and other diseases of the eye.

In particular, we believe that the exposure of the new blood vessels formed during wet type macular degeneration to the beta radiation provides sufficient disruption of the cellular structures of the new blood cell lesions to reverse, prevent, or minimize the progression of the macular degeneration disease process. Such therapy in accordance with the invention can potentially restore visual acuity, extend retention of visual acuity, or slow the progressive loss of visual acuity.

In a preferred embodiment, the surgical device includes a radiotherapy emitting material positioned on the device, such as a cannula, typically a distal end or portion of the cannula. For added safety, the radiotherapy emitting material is preferably shielded. The cannula may be straight or curved. Preferably, to provide access to the macula from a retinotomy peripheral to the macula, the cannula preferably has a bend or curve. Preferably, the beta radiotherapy emitting material is housed in and partially shielded in the distal end of the cannula by a thin wall metal, such as stainless steel, and/or by a thin wall polymer, plastic, or similar material. The shield may also be designed to be retracted to provide a pathway during the exposure period.

The cannula may have a handle extending its proximal end for providing the surgeon with a better grip on the device and for allowing the surgeon to easily reach the surgical site.

The radiotherapy emitting material preferably emits purely beta radiation, however, the radiotherapy emitting material may also be a material that emits very low and insignificant doses of gamma radiation in addition to beta radiation. Any conventional beta radiation emitting materials used in surgical settings may be used in the present device. For example, some suitable pure beta radiation emitting materials may include: $^{206}$Tl (half-life of about 4.20 min), $^{60m}$Co (half-life of about 10.47 min), $^{69}$Zn (half-life of about 55.6 min), $^{209}$Pb (half-life of about 3.253 hours), $^{143}$Pr (half-life of about 13.58 days), $^{32}$P (half-life of about 14.282 days), $^{33}$P (half-life of about 25.34 days), $^{45}$Ca (a half-life of about 165 days), $^{90}$Sr (half-life of about 28.5 years), $^{99}$Tc (half-life of about $2.13 \times 10^5$ years) and $^{36}$S (half-life of about $3.08 \times 10^5$ years).

The duration of radiation emission required during a single treatment for Age Related Macular Degeneration using the device can be quite short, e.g. less than 10 or 15 minutes, or even less than 5 minutes. Typical treatments will range from about 1 to 15 minutes, more typically 2 to ten minutes. Thus, for a single-use device, is it possible to use beta radiation emitting materials having short half-lives. However, in some cases, it is desirable to provide a device with a long shelf-life if, for example, the device is not immediately used or if the device is reusable. Thus, in some cases, it is preferred that the beta radiation emitting material is selected from materials that have a half-life of at least about 2 years. Further, when used for the treatment of Age Related Macular Degeneration, it is preferable that the beta emitting material is selected from materials having an energy ranging from about 50 cGr/sec to about 100 cGr/sec.

The present invention also provides device kits, which preferably comprise one or more of the described beta radiotherapy emitting surgical devices, preferably packaged in sterile condition.

Other aspects and embodiments of the invention are discussed infra.

DETAILED DESCRIPTION OF THE INVENTION

Figure 1:
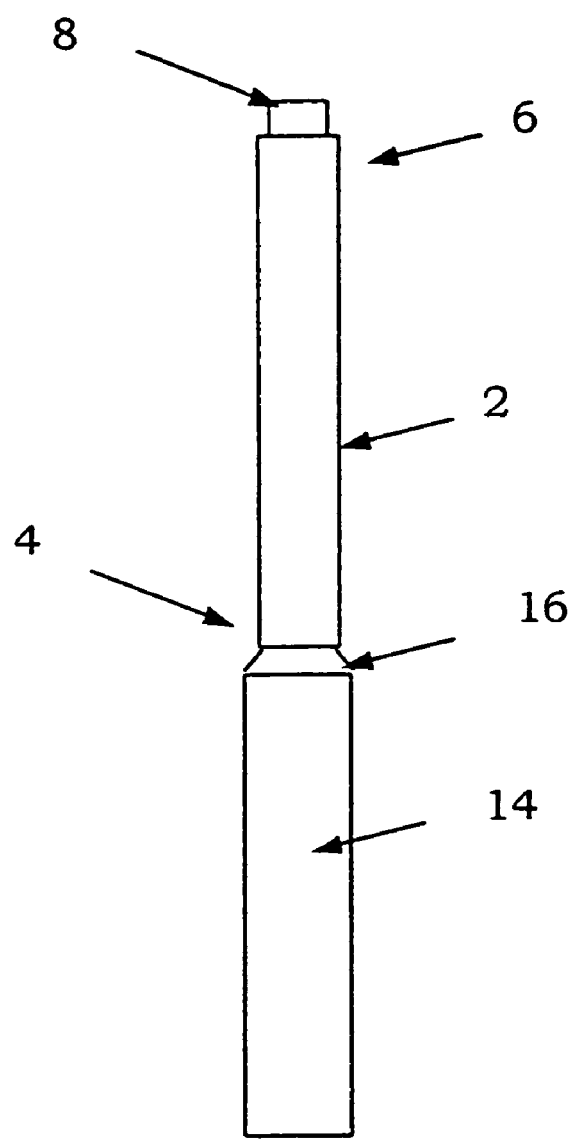
FIG. 1 is an isometric view of one embodiment of the surgical device in accordance with the present invention.
Figure 2:
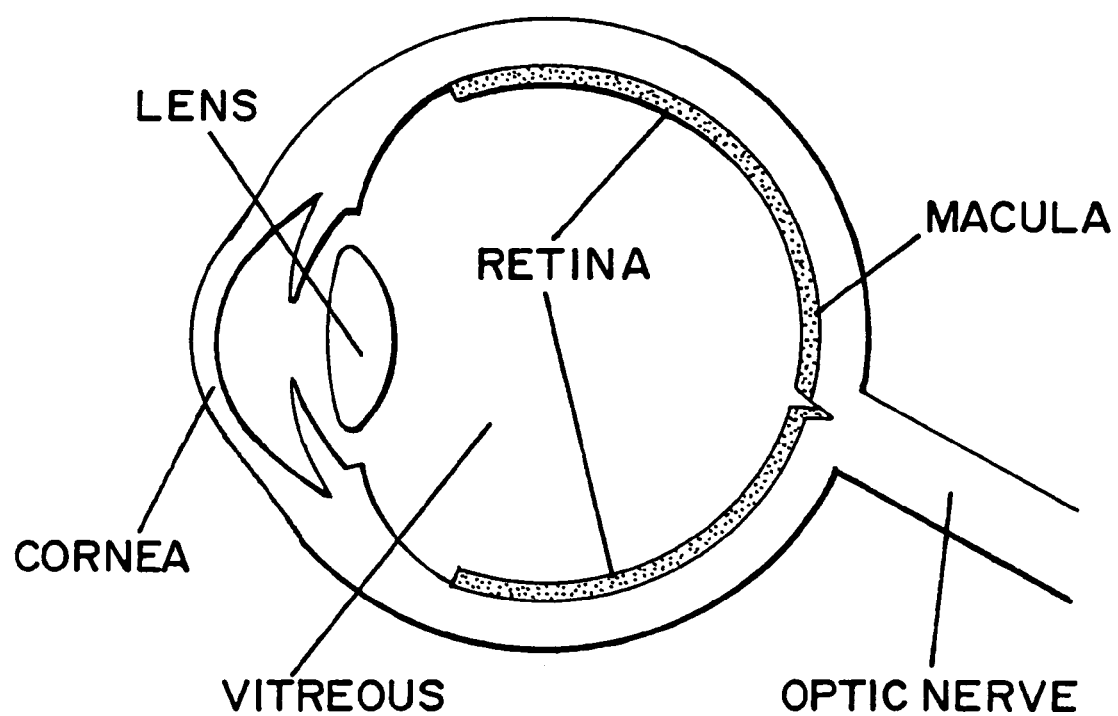
FIG. 2 shows a diagram of a normal, healthy eye.

Referring now to the various figures of the drawing, wherein like reference characters refer to like parts, there is shown in FIG. 1 a view of a surgical device 1 in accordance with the invention.

In a preferred embodiment, the surgical device 1 includes a cannula 2, having a proximal end 4 and a distal end 6. Cannulas are well known and, thus, although described below with reference to a preferred embodiment, the general features (e.g. size, shape, materials) of the cannula 2 may be in accordance with conventional cannulas.

A radiotherapy emitting material 8 is located at the distal end 6 of a cannula 2. The radiotherapy emitting material 8 preferably emits pure beta radiation because beta radiation is easily blocked and, if not shielded, does not penetrate more than about 1–2 mm in human tissue. However, it is possible to use a radiotherapy emitting material 8 that emits very low and insignificant doses of gamma radiation in addition to beta radiation. For example, some suitable pure beta radiation emitting materials may include: $^{206}$Tl (half-life of about 4.20 min), $^{60m}$Co (half-life of about 10.47 min), $^{69}$Zn (half-life of about 55.6 Min), $^{209}$Pb (half-life of about 3.253 hours), $^{143}$Pr (half-life of about 13.58 days), $^{32}$P (half-life of about 14.282 days), $^{33}$P (half-life of about 25.34 days), $^{45}$Ca (half-life of about 165 days), $^{90}$Sr (half-life of about 28.5 years), $^{99}$Te (half-life of about $2.13 \times 10^5$ years), $^{36}$S (half-life of about $3.08 \times 10^5$ years).

The half-life of the beta emitting material may vary depending on the use of the device. For example, when used to treat Age Related Macular Degeneration (AMD), one treatment using the device will typically require radiation emission for a period of time ranging from about two to about ten minutes. Thus, single-use devices that are disposed of between treatments may be fabricated using radiotherapy emitting materials 8 with a relatively short half-life. In some circumstances, it is preferable to provide a device having a long shelf-life. In such circumstances, it is preferable to fabricate the device using radiotherapy emitting materials 8 that are continuously active for a very long time (e.g. with a half-life of at least 2 years).

The energy of the beta emitting material may vary depending on the use of the device. For example, when used to treat Age Related Macular Degeneration (AMD), the beta emitting material is preferably selected from materials having an energy ranging from about 50 cGr/sec to about 100 cGr/sec.

Preferably, for added safety during use of the surgical device 1, the radiotherapy emitting material 8 is at least partially shielded. Because beta radiation is easily shielded, the radiotherapy emitting material 8 may be is housed in and partially shielded in, for example, a thin wall metal, such as stainless steel, or by a thin wall polymer, plastic, or similar material. This may be accomplished by providing a thin wall or shield 10 at the distal end 6 of the cannula 2 about the radiotherapy emitting material 8. In one embodiment, at least a portion the radiotherapy emitting material 8 is housed in and partially shielded in the distal end 6 of the cannula 2. Thus, at least a portion of the distal end 6 of the cannula 2 is fabricated of, for example, a thin wall metal, such as stainless steel, or by a thin wall polymer, plastic, or similar material. Alternatively, if desired, the entire cannula 2 may be fabricated of a thin wall metal, such as stainless steel or similar material, or by a thin wall polymer, plastic, or similar material. The shield 10 may also be designed to be retractable to provide further ease in handling the device and shielding of the radiotherapy emitting material 8 when desired.

To provide a surgeon, patient and others in the operating area with adequate protection from the beta radiation, the thickness of the wall or shield 10 or the thickness of the distal end 6 of the cannula in which the radiotherapy emitting material 8 is housed preferably ranges from about 0.5 to about 3 mm, and more preferably, from about 1 mm to about 2 mm. While thicknesses above about 3 mm may be used, it is believed that thicknesses above about 3 mm will not provide significant additional protection from the beta radiation and would make the surgical device 1 bulky and more difficult to handle.

The cannula 2 may have a handle 14 extending its proximal end 4 for providing the surgeon with a better grip on the surgical device 1 and for allowing the surgeon to easily reach the surgical site. Such handles are known and, thus, the handle 14 of the present invention may be in accordance with conventional handles. The handle may be attached to the cannula 2 by a frictional fit and/or conventional fastening means. The connecting means, such as a hub 16 portion may further be included and designed so as to assist in connecting the cannula 2 to the handle 14 via a frictional fit and, if desired, conventional fastening means may be used to assist the hub 16 in connecting the cannula 2 to the handle 14.

In use, the surgical device 1 is gripped by the handle 14 or a portion of the proximal end 4 of the cannula 2, and the distal end 6 of the cannula 2 with the radiotherapy emitting material 8 is introduced into the surgical site. In contrast to prior methods in which access to the macula is provided by inserting devices between the eyelid and sclera, the present procedure involves making a standard vitrectomy port incision (typically about a 20 gage—approximately 0.89 mm—incision) in the eye to provide access to the macula, located at the back of the eye. The distal end 6 of the cannula 2 and the radiotherapy emitting material 8 are then inserted through the incision towards the macula. This approach will provide the surgeon with a superior ability to locate the radiotherapy emitting material directly in the affected area. This superior positioning approach provides for more effective therapy and enhanced safety for the lens and optic disc. The surgeon will then perform a vitrectomy and pre-detach the macula by injecting saline beneath the retina with a 41 gage needle to gain "direct access" to the sub macular membrane.

The radiotherapy emitting material 8 is preferably positioned within about 1 mm to about 3 mm of the choroidal blood vessels being treated. In some cases, however, the tip may be placed directly on the choroidal blood vessels.

During the procedure, the surgeon can view the interior of the eye using a standard procedure for viewing the macula through the cornea with an illuminated operating microscope and a lens placed on the cornea. The surgeon can alternatively view the interior of the eye by making a second 20 gage incision to provide access for a fiber optic illuminator, which is a standard practice in retinal surgery.

The cannula 2 is preferably elongate in shape to provide easy access to the surgical site. Preferably, the body portion is designed so as to conform with the incision made in the eye, such that as the cannula 2 is inserted in the eye through the incision, the incision molds around the body portion and prevents leakage around the cannula 2. Further, the cannula 2 is preferably designed with a smooth surface so as to prevent further trauma to the eye as it is entered through the incision. In one preferred embodiment, as shown in FIG. 1, the cannula 2 has an elongate cylindrical shape. The cannula 2 may have a substantially uniform cross sectional diameter or may taper. In one preferred embodiment, the cannula 2 tapers towards the distal end 6 to provide precision in placement of the radiotherapy emitting material 8 and to allow for targeted treatment of only the defective, leaking vessels. Although the cannula 2 is depicted as cylindrical in shape, other shapes may be used as desired. Additionally, the cannula 2 may include a bend to provide enhanced access to areas that are difficult to reach. Preferably, to provide access to the macula from a retinotomy peripheral to the macula, the cannula preferably has a curve.

The dimensions of the surgical device 1 may vary depending on its ultimate use. For example, to treat AMD, in cases where the cannula 2 is inserted into the eye through an incision, the length of the cannula 2 would be designed so that the radiotherapy emitting material 8 would reach the appropriate distance to back of the eye while allowing only the cannula 2, and not the hub 16, handle 14 or other apparatus connected to the proximal end 6 of the cannula 2, to enter the incision. As such, the portion of the cannula that enters the incision in the eye preferably has a length ranging from about 28 to about 32 mm. The radiotherapy emitting material 8 portion of the device preferably has a length that ranges from about 2 mm to about 6 mm. More preferably, the length of the radiotherapy emitting material 8 portion of the device ranges from about 2 mm to about 3 mm. The handle 14 of the device preferably ranges from about 3–6 inches to provide a suitable gripping means for the surgeon. If included, the hub 16, which connects the cannula 2 to the handle 14, preferably has a length ranging from about 10 mm to about 12 mm. Further, in applications where a portion of the cannula 2 is inserted into the eye through an incision, the diameter or thickness of the cannula 2 preferably conforms to the size of the incision so that the incision molds around the cannula 2 and prevents leakage around the cannula 2. For example, in preferred embodiments, the diameter or thickness of the cannula 2 ranges from about 0.6 mm to about 1.2 mm. More preferably, the diameter or thickness of the cannula 2 ranges from about 0.8 to about 1.0 mm. However, it is to be understood that the diameter or thickness of the cannula 2 and the length of the portion of the cannula 2 that enters the incision may vary depending on the particular procedure performed, the size of the incision made and the distance from the incision to the treatment area.

The cannula 2 may be fabricated of any conventional materials used in forming similar surgical devices. Preferably, the material is lightweight and strong. Some conventional materials are plastics and stainless steel. Further, because the cannula 2 is inserted in the eye area in some applications, the materials used in forming the cannula 2 must be medically approved for such contact.

The radiotherapy emitting material 8 may be fixedly or removably connected to the distal end 6 of the cannula 2. Known means such as, for example, adhesives may be used to fixedly secure the radiotherapy emitting material 8 to the cannula 2. The radiotherapy emitting material 8 may also be removably connected to the cannula 2 by known means such as, for example, forming the radiotherapy emitting material 8 and the cannula 2 to have corresponding threaded portions that allows removable attachment of the radiotherapy emitting material 8 to the cannula 2 so that the device may be reused by simply sterilizing the cannula 2 with ethelene oxide gas or similar means, and replacing the radiotherapy emitting material 8. Preferably, the entire surgical device 1 is disposed of and replaced between uses to maintain sterility and prevent cross-contamination between uses.

The present invention also includes kits that comprise one or more beta radiotherapy emitting surgical devices of the invention, preferably packaged in sterile condition. Kits of the invention may also include written instructions for use of the beta radiotherapy emitting surgical devices and other components of the kit.

The foregoing description of the invention is merely illustrative thereof, and it is understood that variations and modifications can be effected without departing from the scope or spirit of the invention as set forth in the following claims. For example, although the present invention is described in detail in connection with ophthalmic surgical procedures, particularly in connection with the treatment of AMD, the present invention is not limited to use on the eye. Rather, the present invention may be used on other areas of the body to treat various conditions such as, for example, the prevention of restenosis.

What is claimed is:

1. A method for treating tissue of the human eye, comprising:
   inserting an ionizing radiation source into the vitreous chamber of the eye;
   positioning the ionizing radiation source within the eye at a location spaced from tissue to be treated; and
   exposing the tissue to radiation emitted from the ionizing radiation source.

2. The method in accordance with claim 1 in which the tissue comprises subretinal tissue.

3. The method in accordance with claim 2 in which the subretinal tissue comprises blood vessels.

4. The method in accordance with claim 1 in which the tissue is exposed to a therapeutically effective amount of radiation.

5. The method in accordance with claim 1 in which the tissue is exposed to radiation for a time period between about 1 minute and about 15 minutes.

6. The method in accordance with claim 1 in which the ionizing radiation source has an energy sufficient to provide a dose rate of about 50 cGy/sec to about 100 cGy/sec.

7. The method in accordance with claim 1 in which the radiation emitted from the ionizing radiation source comprises beta radiation.

8. The method in accordance with claim 1 in which the exposing comprises targeting the radiation only at the tissue to be treated.

9. The method in accordance with claim 1 in which the spacing is about 1 mm or more.

10. The method in accordance with claim 1 in which the spacing is about 3 mm or less.

11. The method in accordance with claim 1 in which the spacing is between about 1 mm and about 3 mm.

12. The method in accordance with claim 1 further comprising providing a shield for shielding at least a portion of the ionizing radiation source.

13. The method in accordance with claim 12 in which the shield and the radiation source are relatively movable so as to allow shielding of the ionizing radiation source when desired.

14. The method in accordance with claim 1 in which the exposing comprises positioning the ionizing radiation source so that radiation emitted from the radiation source targets only selected tissue.

15. The method in accordance with claim 1 further comprising withdrawing the ionizing radiation source from the eye.

16. The method in accordance with claim 1 in which the radiation source has an energy sufficient to provide a dose rate at least about 50 cGy/sec.

17. A method of radiotherapy for treating selected tissue of the human eye, comprising:
providing a radiation source delivery cannula having a distal end;
introducing the distal end of the cannula into the vitreous chamber of the human eye;
providing an ionizing radiation source at the distal end of the cannula;
positioning the ionizing radiation source within the eye at a location spaced from the selected tissue; and
exposing the selected tissue to radiation emitted from the ionizing radiation source.

18. The method in accordance with claim 17 in which the selected tissue comprises subretinal tissue.

19. The method in accordance with claim 17 in which the exposing comprises exposing the selected tissue for a time period sufficient to deliver a therapeutically effective amount of radiation.

20. The method in accordance with claim 17 in which the exposing comprises exposing the selected tissue to the radiation for a time period between about 1 minute and about 15 minutes.

21. The method in accordance with claim 17 in which the radiation emitted from the ionizing radiation source comprises beta radiation.

22. The method in accordance with claim 17 in which the exposing comprises targeting the radiation only at the selected tissue.

23. The method in accordance with claim 17 in which the spacing is about 1 mm or more.

24. The method in accordance with claim 17 in which the spacing is about 3 mm or less.

25. The method in accordance with claim 17 in which the positioning comprises positioning the ionizing radiation source at a location that is between about 1 mm and about 3 mm from the selected tissue.

26. The method in accordance with claim 17 further comprising providing a shield for shielding at least a portion of the ionizing radiation source.

27. The method in accordance with claim 26 in which the shield and the radiation source are relatively movable so as to allow shielding of the ionizing radiation source when desired.

28. The method in accordance with claim 17 in which the exposing comprises positioning the ionizing radiation source so that radiation emitted from the radiation source targets only selected tissue.

29. The method in accordance with claim 17 further comprising withdrawing the ionizing radiation source from the eye.

30. The method in accordance with claim 17 in which the radiation source has an energy sufficient to provide a dose rate at least about 50 cGy/sec.

31. A method for treating tissue of the human eye, comprising:
inserting an ionizing radiation source into the vitreous chamber of the eye;
positioning the ionizing radiation source at a location about 3 mm or less from the tissue, the ionizing radiation source having an energy sufficient to provide a dose rate of at least about 50 cGy/sec; and
exposing the tissue to a therapeutically effective amount of radiation emitted from the ionizing radiation source.

32. The method in accordance with claim 31 in which the tissue is exposed to radiation for a time period between about 1 minute and about 15 minutes.

33. The method in accordance with claim 31 in which the radiation emitted from the ionizing radiation source comprises beta radiation.

34. The method in accordance with claim 31 in which the exposing comprises targeting the radiation only at selected tissue.

35. The method in accordance with claim 31 further comprising providing a shield for shielding at least a portion of the ionizing radiation source.

36. The method in accordance with claim 35 in which the shield and the ionizing radiation source are relatively movable so as to allow shielding of the ionizing radiation source when desired.

37. The method in accordance with claim 31 in which the exposing comprises positioning the ionizing radiation source so that radiation emitted from the radiation source targets only selected tissue.

38. The method in accordance with claim 31 further comprising withdrawing the ionizing radiation source from the eye.

* * * * *